United States Patent
Szapiro et al.

(12) 
(10) Patent No.: US 6,602,223 B2
(45) Date of Patent: Aug. 5, 2003

(54) ELASTIC AND SLIDING VALVULAR JOINT, SUITABLE TO WORK IN PRE-FILLED SYRINGES

(76) Inventors: Jaime Luis Szapiro, Viel 759, Buenos Aires (AR); Saul Moreno, Viel 759, Buenos Aires (AR); Leonardo Szames, Viel 759, Buenos Aires (AR)

( * ) Notice: Subject to any disclaimer, the term of this patent is extended or adjusted under 35 U.S.C. 154(b) by 0 days.

(21) Appl. No.: 09/938,961

(22) Filed: Aug. 24, 2001

(65) Prior Publication Data

US 2002/0068910 A1 Jun. 6, 2002

(30) Foreign Application Priority Data

Dec. 5, 2000 (AR) .................................... P000106437

(51) Int. Cl.$^7$ .............................................. A61M 37/00
(52) U.S. Cl. ................... 604/89; 604/82; 604/91
(58) Field of Search ............................ 604/82, 87, 88, 604/89, 90, 91, 218, 246, 247, 249, 256, 167.01, 167.02, 167.03, 167.04

(56) References Cited

U.S. PATENT DOCUMENTS

| | | | | |
|---|---|---|---|---|
| 3,164,303 A | * | 1/1965 | Trautmann | 604/89 |
| 5,298,024 A | * | 3/1994 | Richmond | 604/90 |
| 6,123,685 A | * | 9/2000 | Reynolds | 604/90 |

* cited by examiner

*Primary Examiner*—Michael J. Hayes
*Assistant Examiner*—Kathryn L. Thompson
(74) *Attorney, Agent, or Firm*—Bachman & LaPointe, P.C.

(57) ABSTRACT

A pre-filled syringe having an elastic-sliding valve to produce a hermetic closure inside a pre-filled syringe which keeps the liquid content to be injected totally isolated, in order to prohibit the liquid from coming in contact with the needle or the external air.

5 Claims, 10 Drawing Sheets

ELASTIC AND SLIDING VALVULAR JOINT, SUITABLE TO WORK IN PRE-FILLED SYRINGES

BACKGROUND OF THE INVENTION

The present invention is drawn to pre-filled syringes and, more particularly, an elastic-sliding valve to produce a hermetic closure inside a pre-filled syringe which keeps the liquid content to be injected totally isolated, in order to prohibit the liquid from coming in contact with the needle or the external air.

The characteristic feature of known pre-filled syringes is that they have a cylindrical and hollow main body, with a front section where a communication neck with the injection needle is formed, while inside is a manually movable plunger which extends outward from the back of the main body which is open. All of these known syringes have an inner chamber formed inside the main body, constituting the temporary location of the liquid to be injected. This inner chamber is defined by the cylindrical wall of the main body, the above mentioned front neck where the needle and the active head of the manually movable plunger.

Argentine Patent No. 250.277 discloses a syringe which supports a very special valve plug whose function is to keep the liquid isolated inside of syringe body thus avoiding contact with the needle until the injection is performed. Thus, during the placement of the needle and coupling it to the plugging cone or syringe neck and withdrawal of the protecting sheath to perform the injection, the liquid is kept isolated inside the main body of the syringe, ensuring that these coupling and uncoupling actions do not cause some unwanted loss or spilling. The plug is specially designed to be placed in the neck occluding the same from the outlet mouth. It is important to point out that the plug of the mentioned Patent No. 250.277 is specially designed for the mouth of the syringe neck that faces the injection needle. Due to its special shape the same releases the liquid only when hydraulic pressure is produced from the plunger towards the syringe. This pressure partially removes the plug and the liquid flows.

Accordingly, it would be highly desirable to provide a pre-filled syringe with an elastic-sliding valve which can be selectively located within the syringe so as to be operative with either a single product chamber or, alternatively, a first product chamber and a second product chamber wherein movement of the plunger away from the base opens the elastic-sliding valve member so as to mix the first product and the second product prior to dispensing same.

Accordingly, it is a principal object of the present invention to provide a pre-filled syringe as described above having an elastic-sliding valve selectively located in the syringe for dispensing either a single medicament product or delivering a plurality of medicament products which are mixed together prior to dispensing.

SUMMARY OF THE INVENTION

The elastic-sliding valve of the present invention is specifically designed to isolate the liquid contained in a pre-filled syringe, avoiding its contact with the needle; preferably, the elastic-sliding valve is located within the syringe so as to be effective for dispensing a single medicament product and, alternatively mixing a plurality of medicament products prior to dispensing.

The elastic-sliding valve comprises a discoidal elastic valve member and a cooperative element wherein one of the discoidal elastic valve member and cooperative element is movable relative to the other for opening the elastic-sliding valve for communicating product from an internal chamber of the pre-filled syringe upon movement of the plunger of the syringe toward the base of the syringe. In accordance with a preferred embodiment of the present invention, the discoidal elastic valve member has a peripheral portion which seals on the cylindrical wall and a disklike central portion. The cooperative element likewise comprises a peripheral portion for sealing on the cylindrical wall and includes a central portion. One of the central portions includes a closure element and the other of the central portion includes a fluid passage which receives the closure element when the elastic-sliding valve is in the closed position. In accordance with the preferred embodiment, the central portion of the discoidal elastic valve member is provided with the closure element and the central portion of the discoidal valve element further includes a plurality of openings distributed around the closure element for communicating product. The elastic-sliding valve may be located adjacent to the base of the syringe and in that position is useful for dispensing a single medicament product when the elastic-sliding valve is opened upon movement of the plunger away from the base and product is dispensed through the open valve upon forward movement of the plunger toward the base. Alternatively, the elastic-sliding valve divides the internal chamber into a first product chamber and a second product chamber. Movement of the plunger away from the base results in the opening of the elastic-sliding valve member so as to mix the product in the first chamber with the product in the second chamber prior to feeding the product upon movement of the plunger forward toward the base.

BRIEF DESCRIPTION OF THE DRAWINGS

The details of the present invention will be made more clear from a consideration of the following detailed drawings which are merely illustrative of the intentions of the basic concept of the present invention.

DETAILED DESCRIPTION OF PREFERRED EMBODIMENTS

Figure 1:
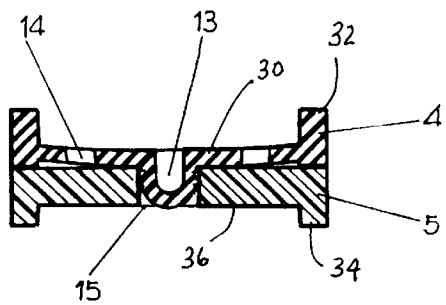
FIG. 1 is a sectional view showing the elastic-sliding valve of the present invention.
Figure 3:
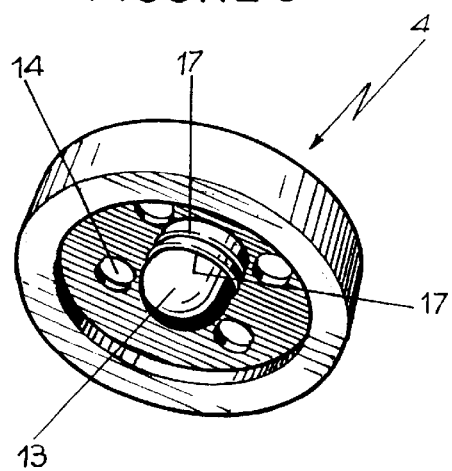
FIG. 3 is a perspective view of the discoidal elastic valve member.

With reference to FIG. 1, the elastic-sliding valve of the present invention is illustrated and includes a discoidal elastic valve member 4 and a cooperative valve member 5. The discoidal elastic valve member 4 has a peripheral ring portion 32 and a disklike central portion 30. The disklike central portion 30 carries a hollow stub 13 which acts as a closure element. The stub 13 may include a ridged surface 17 as shown in FIG. 3. The central portion 30 further includes a plurality of holes or openings distributed around the closure member for reasons to be made clear hereinbelow.

Figure 2:
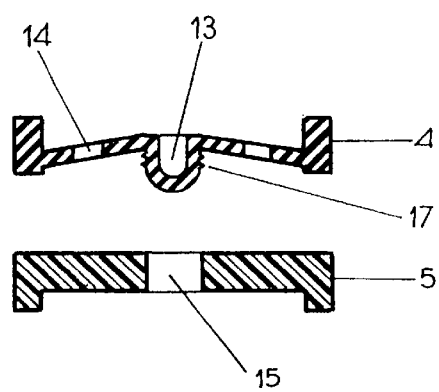
FIG. 2 is a sectional view similar to FIG. 1 showing the valve in the open position.
Figure 4:
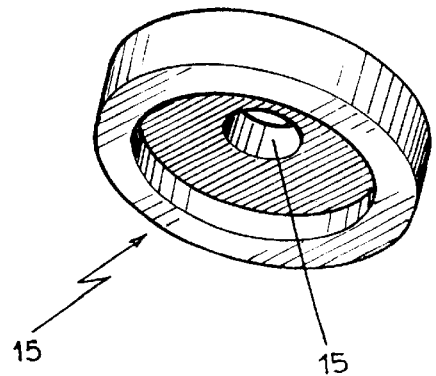
FIG. 4 is a perspective view of the cooperative element.

The cooperative element likewise has a peripheral portion 34 and a central portion 36. The central portion 36 is provided with a fluid passage 15 which receives the closure element 13 of the discoidal valve member 14 when the valve is in the closed position as shown in FIG. 1. FIG. 4 is a perspective view of the cooperative element 5. FIG. 2 illustrates the elastic-sliding valve in the open position.

With reference to FIGS. 5–9, the operation of the elastic-sliding valve of the present invention will be discussed in detail as it is applied to a pre-filled syringe for a plurality of medicament products.

Figure 5:
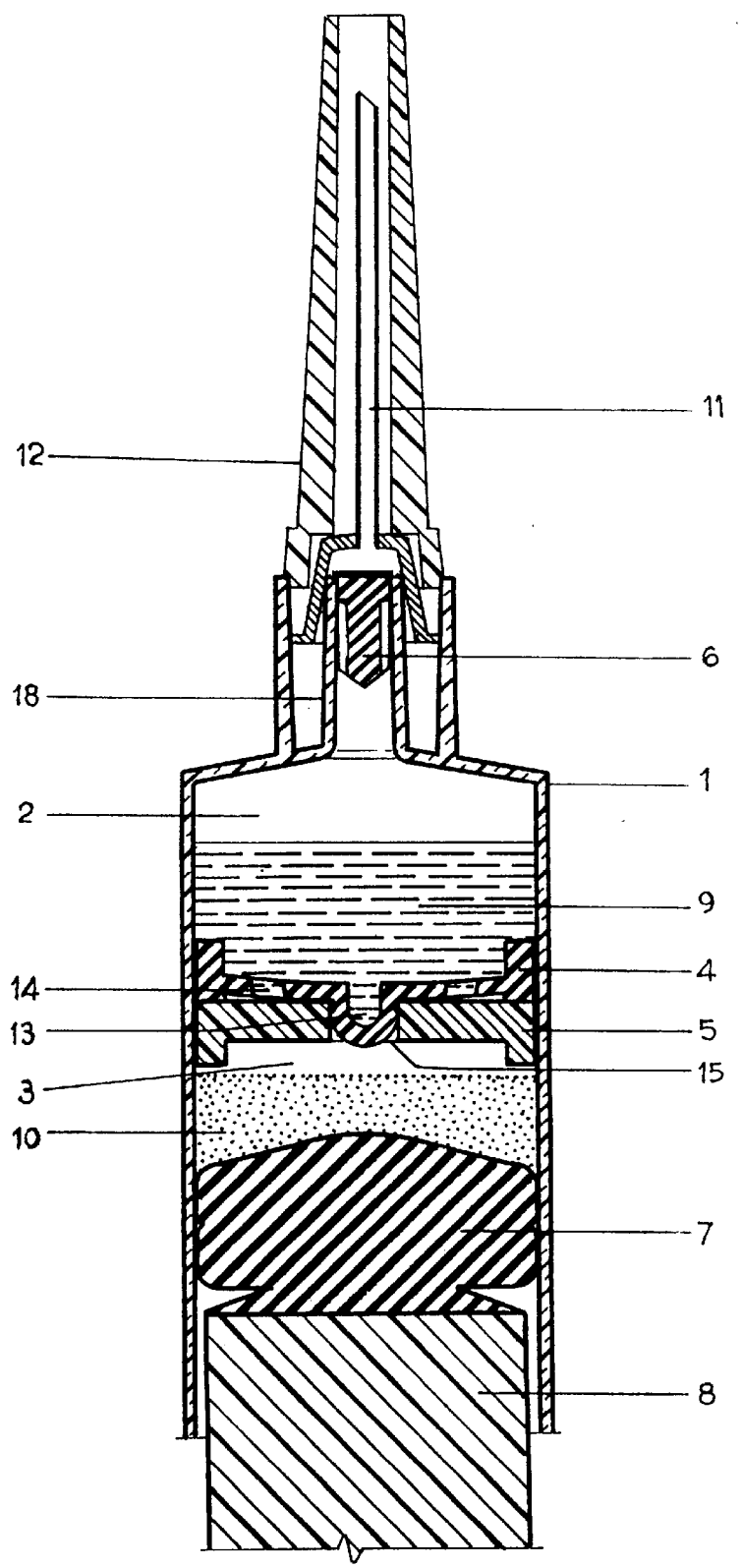
FIG. 5 is a sectional view of a pre-filled syringe wherein the elastic-sliding valve is located to provide a first product chamber and a second product chamber, the elastic-sliding valve being in the closed position.

With reference to FIG. 5, the elastic-sliding valve comprising the discoidal elastic valve member 4 and the cooperative element 5 is located in the pre-filled syringe on the cylindrical wall 1 at an intermediate location so as to divide the internal chamber defined by the cylindrical wall into a first product chamber 2 and a second product chamber 3.

With reference to FIG. 5, the pre-filled syringe having the cylindrical wall 1 is connected to a base portion 40 and includes movable plunger 7, 8 which together with the cylindrical wall 1 and the base 40 defines the internal chamber of the pre-filled syringe. The elastic-sliding valve divides the internal chamber, as noted above, into a first product chamber 2 and a second product chamber 3 wherein the products are illustrated respectively by reference numerals 9 and 10. The base communicates through outlet 18' with a passage 18 to a needle 11 which may be covered, as is known in the art, with a protective sheath 12. A plug valve 6 is included in the passage so as to insure no inadvertent leakage and is designed as known in the prior art so as to be movable to an open position for communicating flow from the internal chamber to the needle 11 upon application of pressure by forward movement of the plunger 7, 8 toward the base 40.

Figure 6:
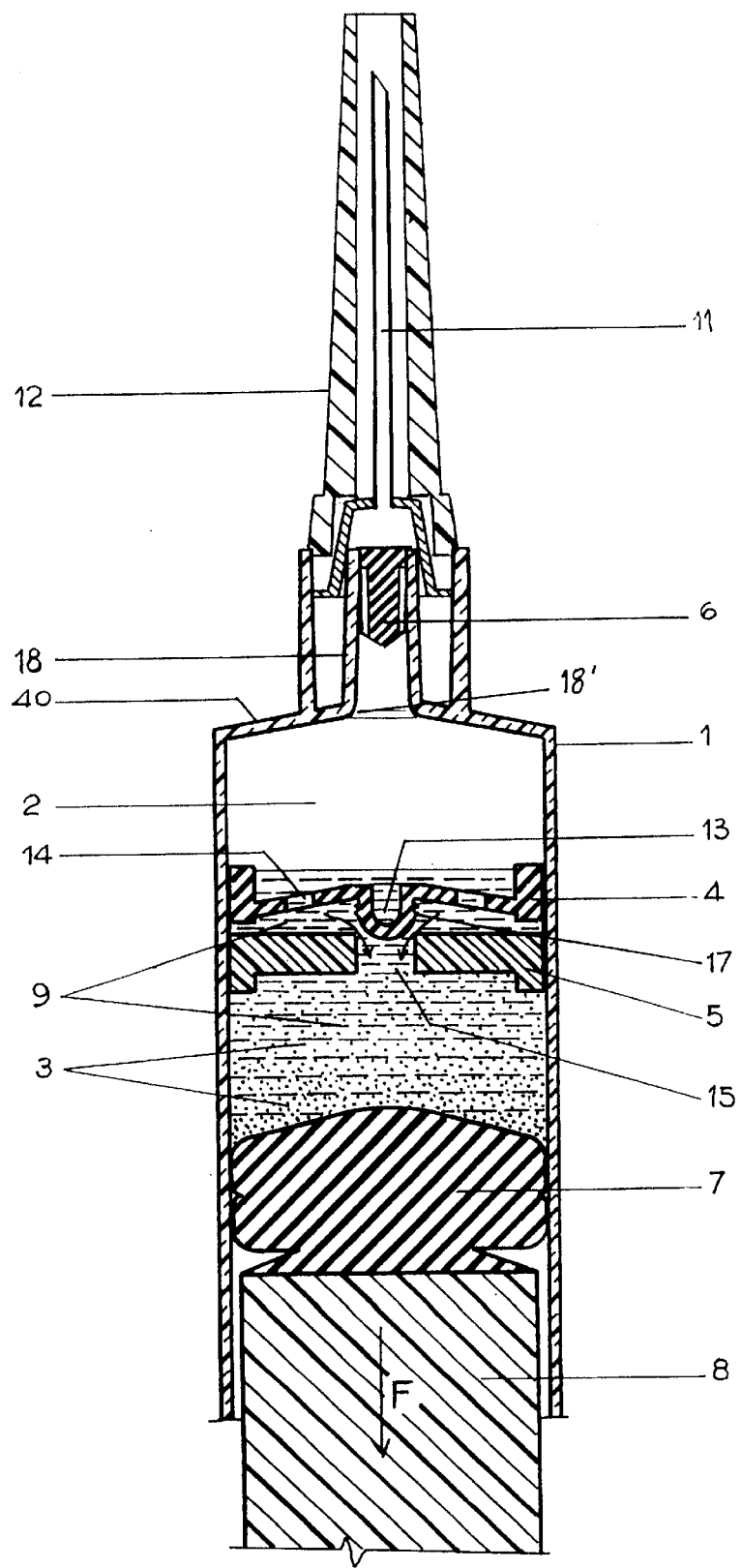
FIG. 6 is a sectional view as in FIG. 5 wherein the plunger is moved away from the base so as to open the elastic-sliding valve for mixing the product in the first chamber with the product in the second chamber.
Figure 7:
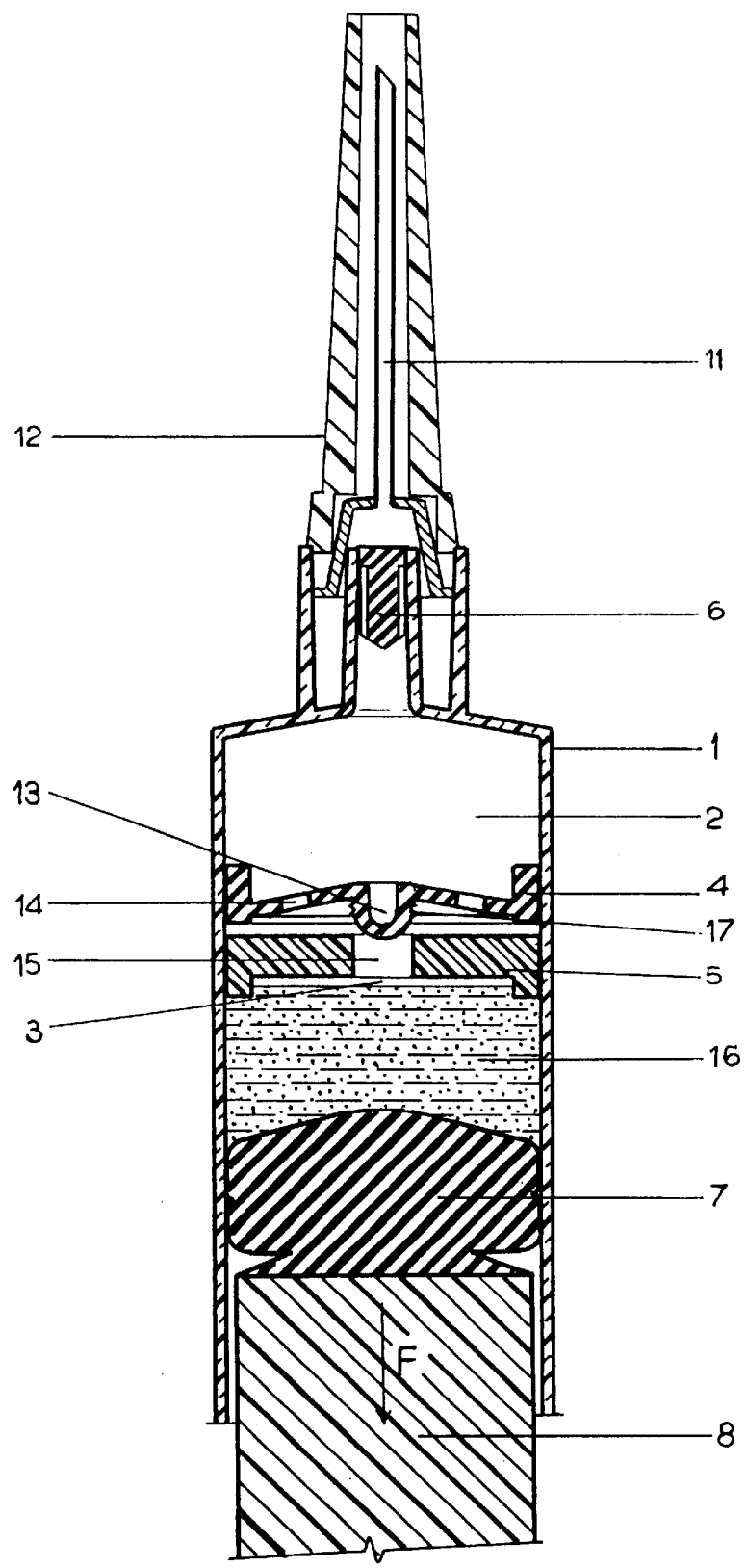
FIG. 7 is a view similar to FIG. 6 showing complete mixing of the two products.

With reference to FIG. 6, as the plunger 7, 8 is drawn back in the direction F away from the base 40, the cooperative element 5 slides on the cylindrical wall under the suction force of the plunger thereby removing closure element 13 from fluid passage 15. This allows the product in product chamber 2 to be drawn through passages 14 and 15 in elements 4 and 5 respectively into the second product chamber 3 where the two products may be intermixed. FIG. 7 shows the completion of the mixing step.

Figure 8:
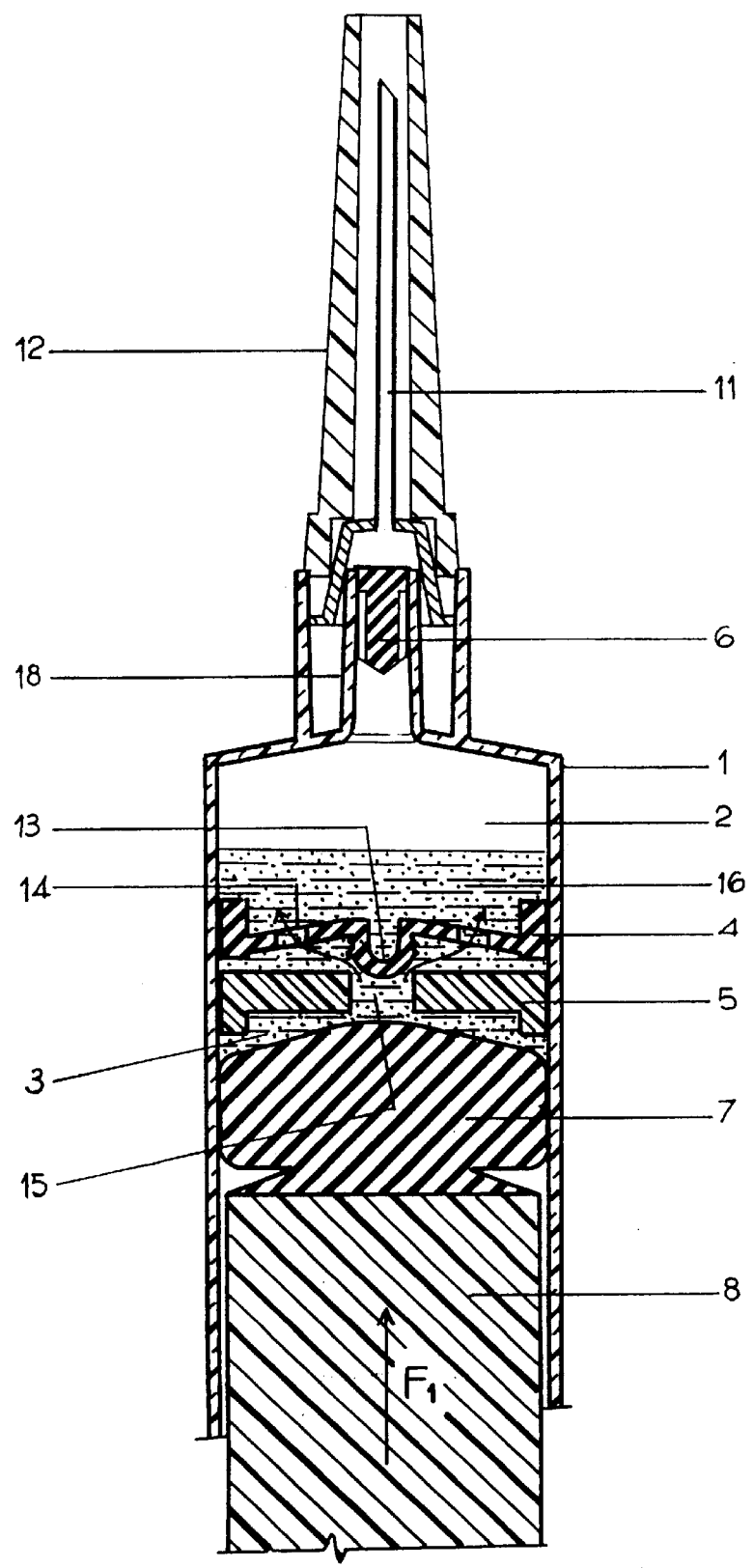
FIG. 8 is a sectional view similar to FIG. 7 wherein the plunger is being moved toward the base for dispensing the mixed product toward the needle passage.
Figure 9:
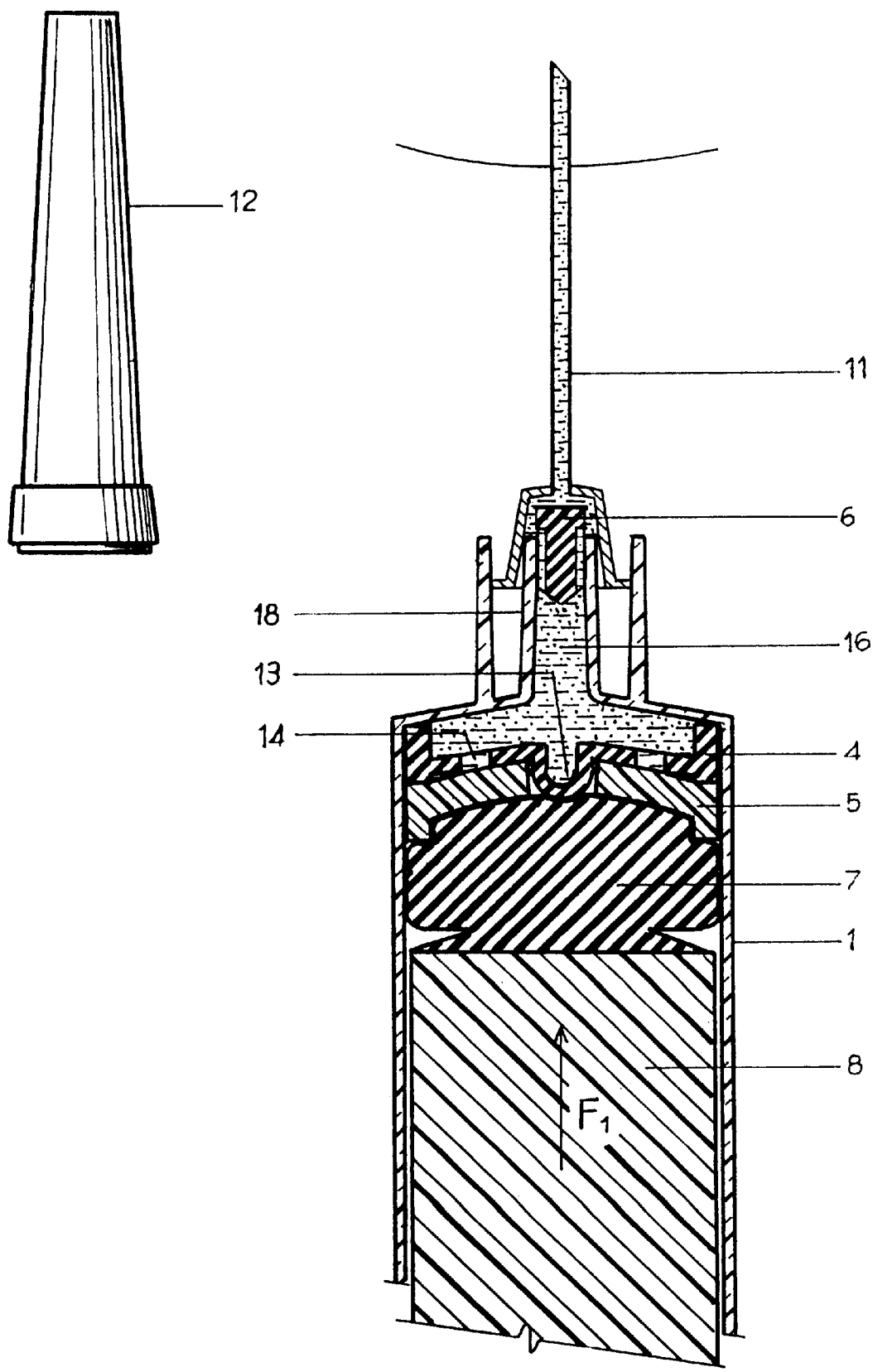
FIG. 9 is a sectional view similar to FIG. 8 showing the plunger in its complete forward position.

With reference to FIG. 8, the plunger is then moved forward so as to move the mixed medicament product from the second chamber 3 again through passages 5 and 14 in elements 5 and 4 into first product chamber 2 and thus into passage 18 wherein the pressure unseats plug valve 6 so as to allow the medicament product to proceed to the needle portion 11 of the pre-filled syringe. FIG. 9 shows the position of the valve members upon complete movement of the plunger 7, 8 toward the base 40 wherein all of the medicament is dispensed and the closure element 13 is again seated in the opening 15.

Figure 10:
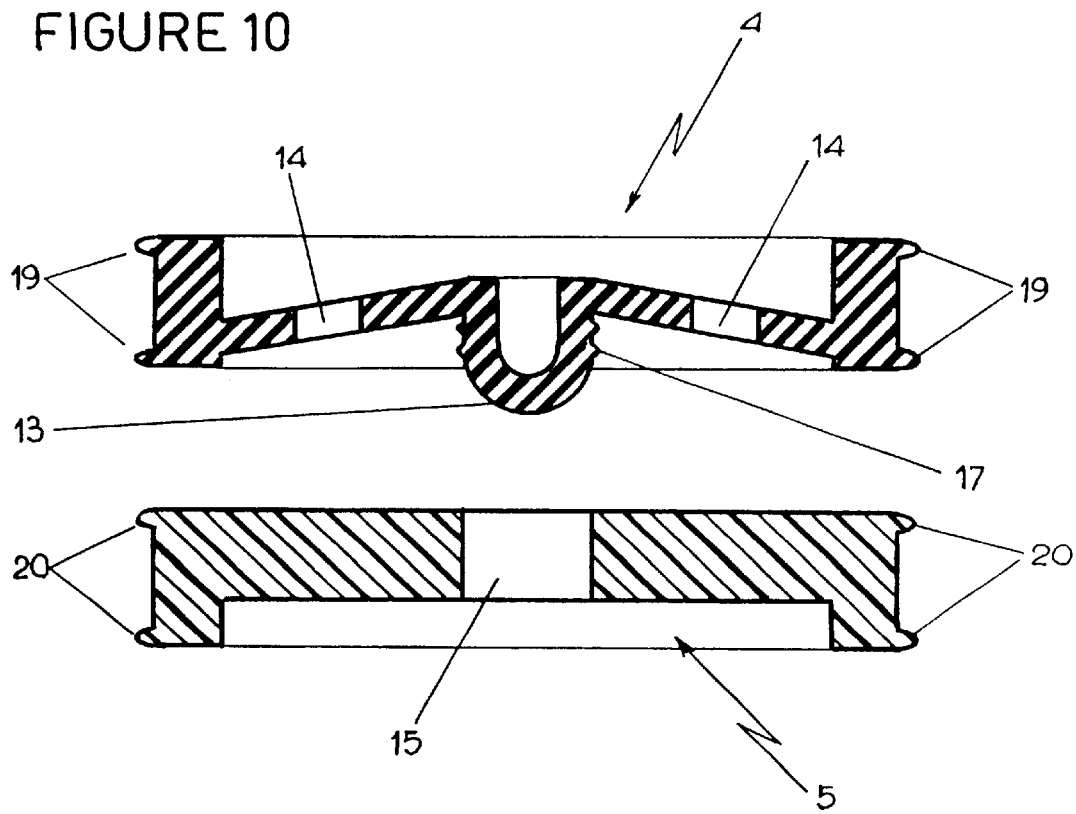
FIG. 10 is an alternative embodiment of the elastic-sliding valve similar to FIG. 2.
Figure 11:
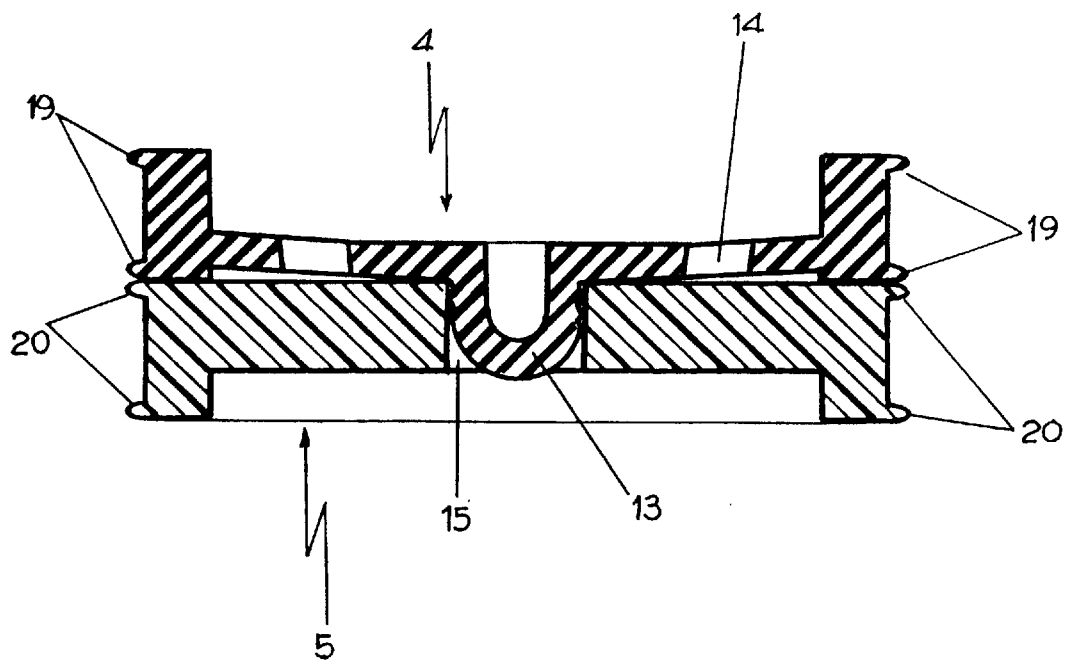
FIG. 11 is an alternative embodiment of FIG. 10 showing the valve in the closed position.

FIGS. 10 and 11 show a modified form of the elastic-sliding valve of the present invention which includes ring flanges on each of the peripheral portions of the elements 4 and 5 of the elastic-sliding valve of the present invention. This reduces contact surface between the elements and the cylindrical wall which makes sliding movement of the element 5 as well as movement of the element 4 easier without loss of air tightness.

Figure 12:
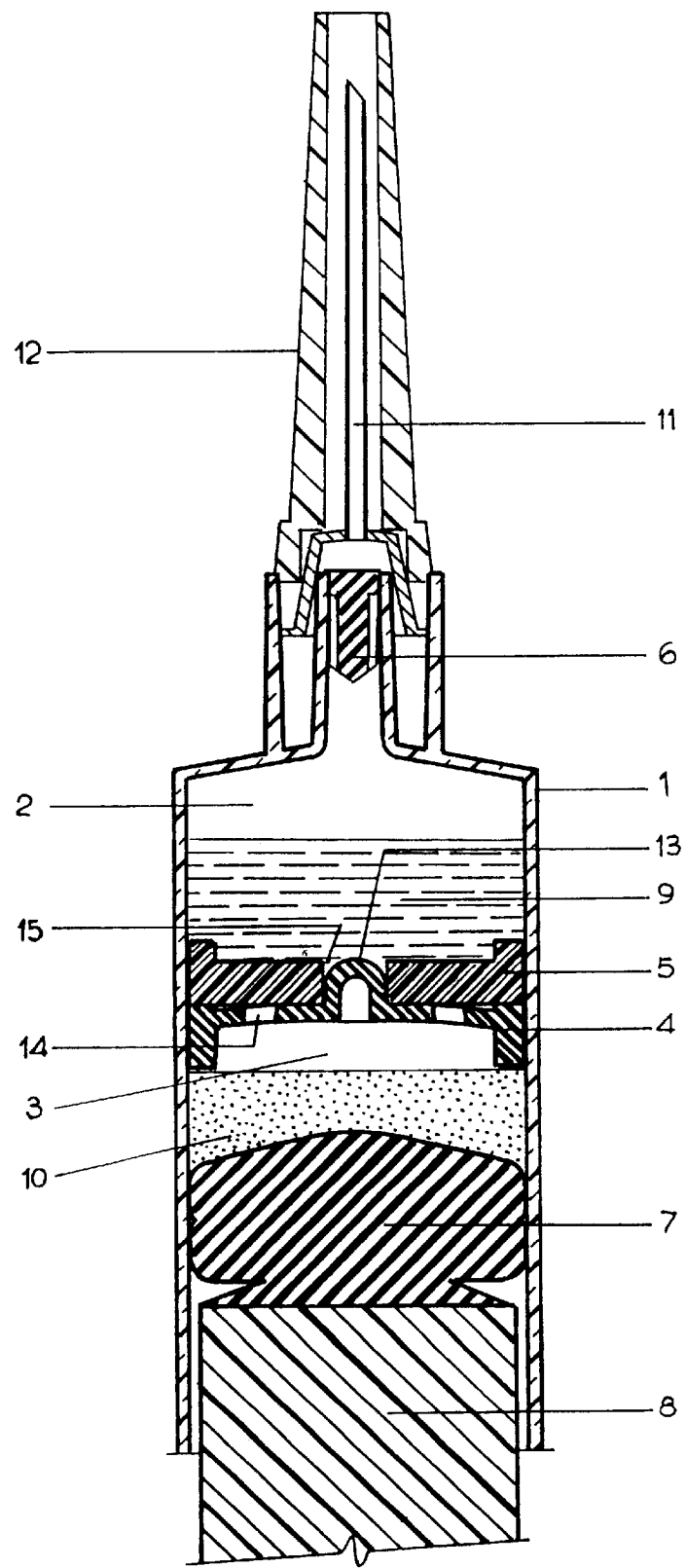
FIG. 12 shows an alternative embodiment of the present invention wherein the location of the discoidal valve member and the cooperative element have been reversed with respect to FIG. 5.
Figure 13:
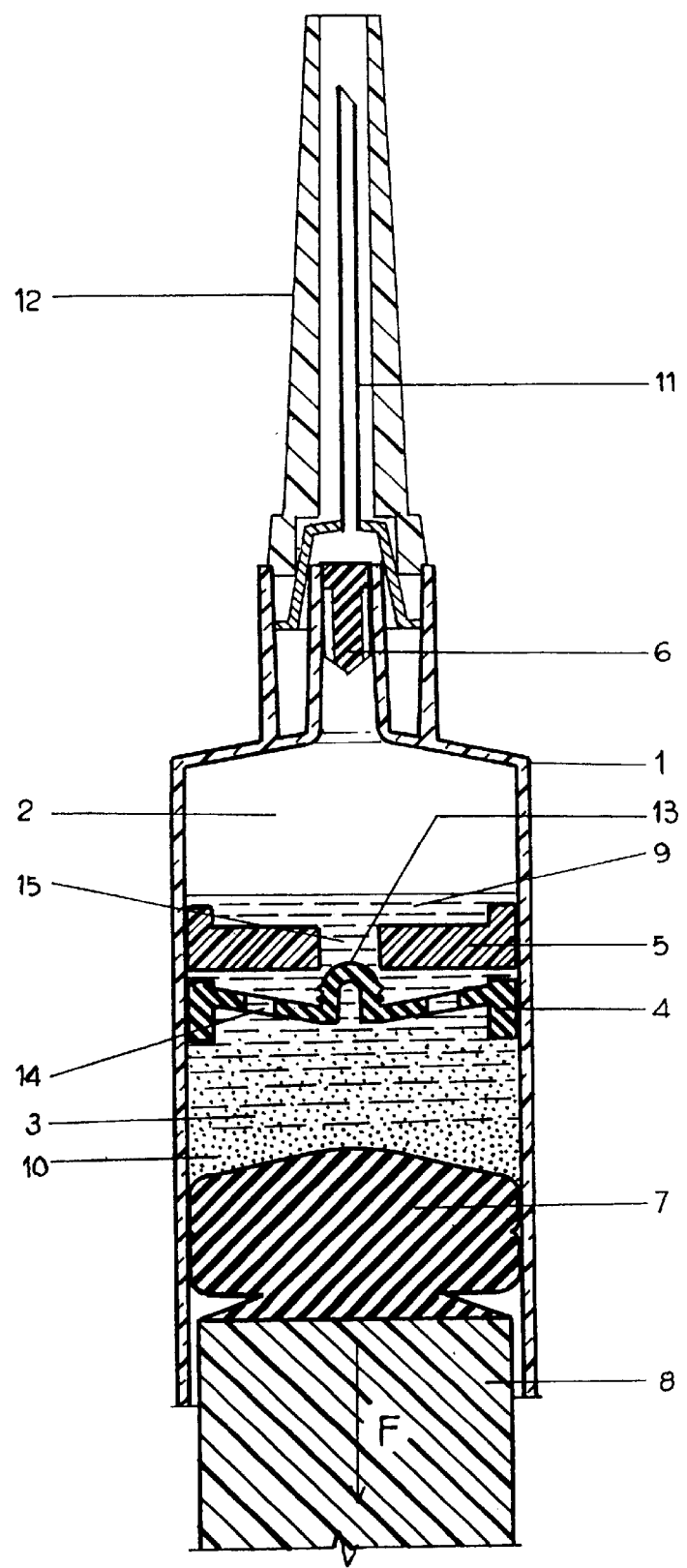
FIG. 13 shows the valve of FIG. 12 in the open position upon movement of the plunger away from the base.

FIGS. 12 and 13 show the elastic-sliding valve member located in position similar to FIG. 5 wherein the positions of the elements 4, 5 have been reversed such that on the suction stroke of the plunger 7, 8, as shown in FIG. 13, the discoidal elastic valve member 4 slides so as to remove the closure element 13 from the passage 15.

Figure 14:
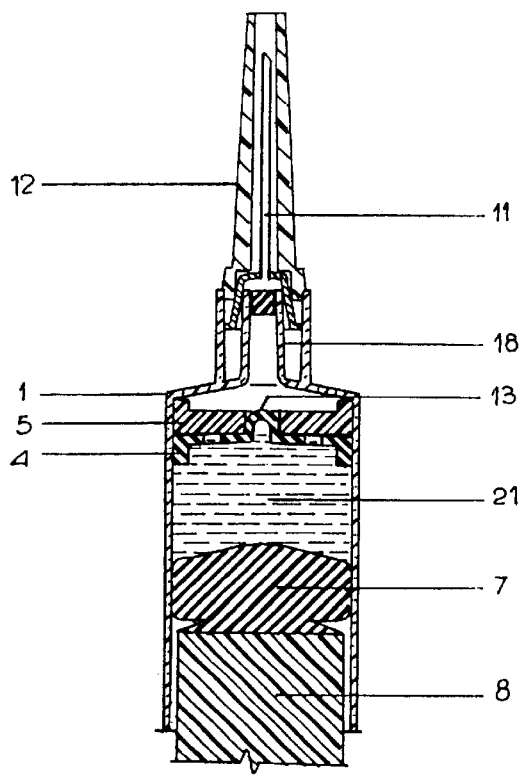
FIG. 14 shows the location of the elastic-sliding valve adjacent to the base for dispensing a single product.
Figure 15:
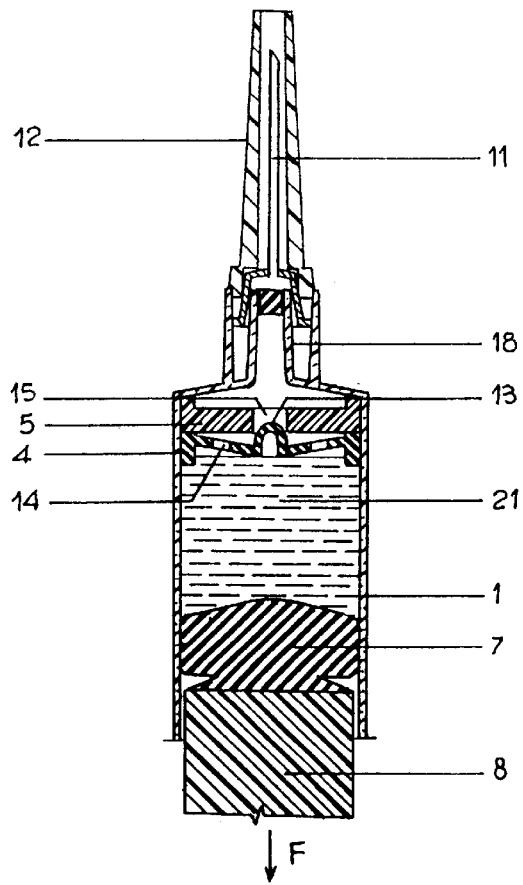
FIG. 15 shows the valve of FIG. 14 in the open position.

FIGS. 14 and 15 show the location of the elastic-sliding valve of the present invention adjacent to the base which is the preferred location when dispensing a single medicament product from the internal chamber.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A pre-filled syringe having a cylindrical wall connected to a base and a moveable plunger which together with the cylindrical wall and the base define an internal chamber for a liquid product to be dispensed, the base being provided with an outlet communicating with a passage for feeding product from the internal chamber between the plunger and base to define a first product chamber between the base and the elastic-sliding valve and a second product chamber between the elastic-sliding valve and the plunger, through the passage to a needle upon movement of the plunger toward the base, the improvement which comprises an elastic-sliding valve positioned within the internal chamber, said elastic-sliding valve comprising a discoidal elastic valve member and a cooperative element wherein one of said discoidal elastic valve member and cooperative element is moveable relative to the other for opening the elastic-sliding valve for communicating product from the internal chamber through the passage upon movement of the plunger toward the base wherein movement of the plunger away from the base results in opening of the elastic-sliding valve member so as to mix the product in the first chamber with the product in the second chamber prior to feeding product through the passage into the needle upon movement of the plunger toward the base.

2. A syringe according to claim 1, wherein the discoidal elastic valve member has a peripheral portion with seals on the cylindrical wall and a disklike central portion, said cooperative element comprises a peripheral portion for sealing on the cylindrical wall and a central portion, wherein one of the central portions includes a closure element and the other of the central portions includes a fluid passage which receives the closure element when the elastic-sliding valve is in the closed position.

3. A syringe according to claim 2, wherein the central portion of the discoidal elastic valve member is provided with the closure element and further includes a plurality of openings distributed around the closure element.

4. A syringe according to claim 3, wherein said elastic-sliding valve is located adjacent to the base of the syringe and said elastic-sliding valve is opened upon movement of the plunger from the base.

5. A syringe according to claim 1, wherein both the discoidal elastic valve member and the cooperative element are separate from the plunger and free floating within the internal chamber.

* * * * *